US006590073B2

(12) United States Patent
Dalder et al.

(10) Patent No.: US 6,590,073 B2
(45) Date of Patent: Jul. 8, 2003

(54) FORMATION AND ANION-EXCHANGE OF CRYSTALLINE ECHINOCANDIN AMMONIUM SALTS

(75) Inventors: Brian Weston Dalder, West Lafayette, IN (US); Michael Anthony Dotlich, Lafayette, IN (US); Neil John Kallman, Lafayette, IN (US); Samuel Dean Larsen, West Lafayette, IN (US); Sharon Van Den Berghe Snorek, Lafayette, IN (US); Jeffrey Thomas Vicenzi, Brownsburg, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/944,309

(22) Filed: Aug. 30, 2001

(65) Prior Publication Data

US 2002/0161176 A1 Oct. 31, 2002

Related U.S. Application Data

(63) Continuation of application No. PCT/US00/05494, filed on Mar. 2, 2000.
(60) Provisional application No. 60/123,073, filed on Mar. 3, 1999.

(51) Int. Cl.$^7$ .......................... A61K 38/12; C07K 7/50; C07K 1/36
(52) U.S. Cl. ..................... 530/317; 530/344; 530/345; 530/300; 514/11; 514/9; 514/2; 435/71.1
(58) Field of Search .............................. 530/317, 300, 530/344, 345; 514/11, 9, 2; 435/71.1

(56) References Cited

U.S. PATENT DOCUMENTS

| 3,293,482 A | 12/1966 | Wolkstein |
| 3,978,210 A | 8/1976 | Mizuno et al. |
| 4,293,482 A | 10/1981 | Abbott et al. |
| 4,293,483 A | 10/1981 | Debono |
| 4,293,489 A | 10/1981 | Debono |
| 4,299,763 A | 11/1981 | Abbott et al. |
| 4,304,716 A | 12/1981 | Abbott et al. |
| 4,320,052 A | 3/1982 | Abbott et al. |
| 4,876,241 A | 10/1989 | Feldman et al. |
| 5,166,135 A | 11/1992 | Schmatz |
| 5,198,421 A | 3/1993 | Chen et al. |
| 5,541,160 A | 7/1996 | Balkovec et al. |
| 5,932,543 A | 8/1999 | Burkhardt et al. |
| 5,965,525 A | 10/1999 | Burkhardt et al. |

FOREIGN PATENT DOCUMENTS

| EP | 0 031 221 A1 | 7/1981 | |
| EP | 0031221 | * 7/1981 | .......... A61K/37/02 |
| EP | 0 359 529 A1 | 3/1990 | |
| EP | 0 359 529 B1 | 3/1990 | |
| EP | 0 447 186 A1 | 9/1991 | |
| EP | 0 448 353 A2 | 9/1991 | |
| EP | 0 448 353 A3 | 9/1991 | |
| EP | 0 460 882 A2 | 12/1991 | |
| EP | 0 460 882 A3 | 12/1991 | |
| EP | 0 460 882 B1 | 12/1991 | |
| EP | 0 462 531 A2 | 12/1991 | |
| EP | 0 462 531 B1 | 12/1991 | |
| EP | 0 561 639 A1 | 9/1993 | |
| EP | 0 561 639 B1 | 9/1993 | |
| WO | WO 96/31228 A1 | 10/1996 | |
| WO | WO 96/37509 A1 | 11/1996 | |
| WO | WO 96/37510 A1 | 11/1996 | |
| WO | WO 96/37511 A1 | 11/1996 | |
| WO | WO 96/37512 A1 | 11/1996 | |
| WO | WO 97/05163 A1 | 2/1997 | |
| WO | WO 97/27864 A1 | 8/1997 | |
| WO | WO 99/06062 A1 | 2/1999 | |
| WO | WO 99/43337 A1 | 9/1999 | |
| WO | WO 00/11023 A2 | 3/2000 | |
| WO | WO 00/11023 A3 | 3/2000 | |
| WO | WO 00/12540 A1 | 3/2000 | |
| WO | WO 00/34315 A2 | 6/2000 | |
| WO | WO 00/34315 A3 | 6/2000 | |
| WO | WO 00/35944 A1 | 6/2000 | |
| WO | WO 00/35945 A1 | 6/2000 | |
| WO | WO 00/51564 A1 | 9/2000 | |
| WO | WO 00/51567 A1 | 9/2000 | |
| WO | WO 00/52036 A1 | 9/2000 | |
| WO | WO 00/52037 A1 | 9/2000 | |

OTHER PUBLICATIONS

Ibrahim, F. S. et al., (1995) "The Effect of pH, sugars and calcium ion concentration on the thermal stability of whey proteins" *Egyptian J. Dairy Sci.* 23:177–178.
Nail, S. L. and Gatlin, L. A. (1993) "Chapter 3: Freeze drying: Principles and practice" *Pharmaceutical Dosage Forms*, Parenteral Medications, vol. 2, 2nd Edition, edited by Kenneth, E. A. et al., Marcel Dekker, Inc., pp. 163–233.
Etter, M.C. and Baures, P.W. (1988) "Triphenylphosphine Oxide as a Crystallization Aid," *J. Am. Chem. Soc.* 110:639–640.

* cited by examiner

Primary Examiner—Christopher S. F. Low
Assistant Examiner—Chih-Min Kam
(74) Attorney, Agent, or Firm—Morrison & Foerster LLP

(57) ABSTRACT

A method is described for forming a crystalline Echinocandin nucleus salt from its mixed broth and/or partially purified process streams by the steps of nanofiltration to form a concentrate, addition of an aldehyde derivatizing agent which interacts with an aldehyde impurity, addition of an acid/metal salt to form a solubilized echinocandin nucleus salt having the desired anion, and subsequent cooling of the mixture to crystallize the salt.

10 Claims, No Drawings

FORMATION AND ANION-EXCHANGE OF CRYSTALLINE ECHINOCANDIN AMMONIUM SALTS

CROSS-REFERENCE TO RELATED APPLICATIONS

This application is a continuation of International Patent Application No. PCT/US00/05494, filed on Mar. 2, 2000, which claims priority to U.S. Provisional Patent Application Ser. No. 60/123,073, filed on Mar. 3, 1999, the contents of each of which are incorporated herein by reference in their entirety.

FIELD OF THE INVENTION

The present invention relates to a process for formation and anion-exchange of crystalline salts of an echinocandin nucleus, in particular, salts of an Echinocandin B nucleus.

BACKGROUND OF THE INVENTION

Echinocandin cyclopeptides are natural antifungal products. Included in the Echinocandin cyclopeptide family are natural products such as Echinocandin B (ECB), Echinocandin C, Aculeacin A$\gamma$, Mulundocandin, Sporiofungin A, Pneumocandin $A_0$, WF11899A, and Pneumocandin $B_0$. These are typically produced by culturing various microorganisms. For example, Echinocandin B is produced from the fermentation of the fungus, *Aspergillus Nidulans*.

In the search for more active materials, the natural products have been modified in a variety of ways. One of the most common has been replacement of the N-acyl side chain on the natural product to produce a semi-synthetic derivative. For example, U.S. Pat. Nos. 4,293,489; 4,320,052; 5,166,135; and 5,541,160; and EP 359529; 448353; 447186; 462531; and 561639 describe a variety of N-acyl derivatized Echinocandin compounds with varying degrees of antifungal activity.

The N-acyl derivatives are produced by deacylating the natural product followed by reacylation with a different acyl group. Deacylation is typically achieved by means of an enzyme (e.g., deacylase enzyme). The deacylase enzyme may be obtained from the microorganism *Actinoplanes utahensis* or Pseudomonas species (see i.e., U.S. Pat. Nos. 4,293,482 and 4,304,716; and EP 460,882). The deacylated compound is typically referred to as the nucleus of the corresponding natural product (e.g., the deacylated product of Echinocandin B is referred to as the Echinocandin B nucleus (ECBN)). Unfortunately, both the acylated and unacylated products are difficult to purify due to their limited solubility and amorphous state. In addition, the free amino compound (e.g., ECBN) is generally unstable and subject to ring opening.

It is well-known in the art that crystalline materials in general are easier to purify than their amorphous counterparts. Hence, it is desirable to produce cyclopeptide compounds in their crystalline state to obtain optimal purity. Since the potency of the final pharmaceutical product is dependent upon the purity of the intermediates used to make the final product, improvements in purity at any stage of the manufacturing process is highly desirable. Ideally, the contaminants are removed at the earliest stage possible in the manufacturing process. Hence, there is a need for a process that simplifies and improves the purification of cyclopeptide compounds containing a free amino group prior to subsequent attachment of an amino substituent.

BRIEF SUMMARY OF THE INVENTION

The present invention provides a method for forming a crystalline echinocandin nucleus salt from its mixed broth or partially purified process streams by the steps of (i) concentrating a solution comprising an echinocandin nucleus or amorphous salt thereof, an aldehyde impurity and a solvent by means of a nanofiltration process to form a concentrate; (ii) adding an aldehyde derivatizing agent; (iii) adjusting the pH to a value less than 4.0 (preferably between about 2.0 and about 3.0); (iv) adding an acid or metal salt; and (v) cooling the concentrate to crystallize an echinocandin nucleus salt having an anion corresponding to the anion of the acid or metal salt added in step (iv). A seed crystal may optionally be added to initiate crystallization.

In another embodiment of the present invention, a process for exchanging the anion of an Echinocandin ammonium salt (including simple derivatives thereof) is provided as well as various forms of crystalline echinocandin nucleus salts.

DEFINITIONS

"Echinocandin compounds" refers to compounds having the following general structure including any simple derivatives thereof:

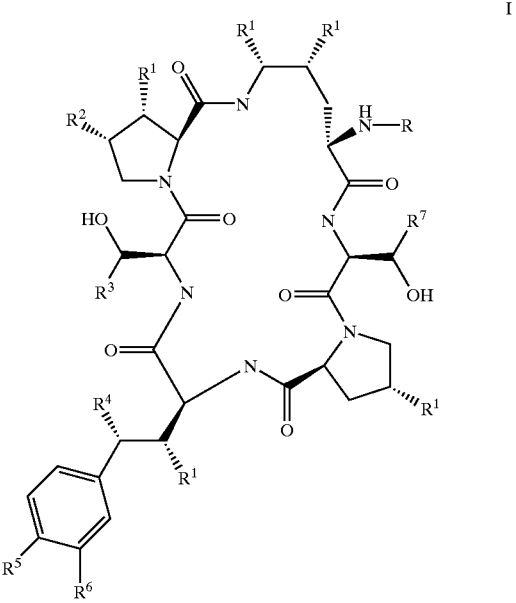

wherein R is a hydrogen or —C(O)R' where R' is an alkyl group, an alkenyl group, an alkynyl group, an aryl group, or heteroaryl group; $R^1$ is —H or —OH; $R^2$ is —H, —NH$_2$ or —CH$_3$; $R^3$ is —H, —CH$_3$, —CH$_2$CONH$_2$ or —CH$_2$CH$_2$NH$_2$; $R^4$ is —H or —OH; $R^5$ is —OH, —OSO$_3$H, or —OPO$_2$HR$^a$, where R$^a$ is hydroxy, C$_1$–C$_6$ alkyl, C$_1$–C$_6$ alkoxy, phenyl, phenoxy, p-halophenyl, p-halophenoxy, p-nitrophenyl, p-nitrophenoxy, benzyl, benzyloxy, p-halobenzyl, p-halobenzyloxy, p-nitrobenzyl, or p-nitrobenzyloxy; $R^6$ is —H, —OH, or —OSO$_3$H; $R^7$ is —H or —CH$_3$; and pharmaceutically acceptable salts, esters, hydrates or solvates thereof. Also included within the meaning of echinocandin are the various enantomeric forms of structure I illustrated above even though specific chiral centers are depicted. "Echinocandin nucleus" refers to the deacylated Echinocandin compound where R is a hydrogen. "ECBN" refers to the Echinocandin B nucleus where R1, R4 and R5 are hydroxyl groups, R2, R3, and R7 are methyl groups; and R and R6 are hydrogens.

"Alkyl" refers to a hydrocarbon radical of the general formula C$_n$H$_{2n+1}$, containing from 1 to 30 carbon atoms unless otherwise indicated. The alkane radical may be straight (e.g. methyl, ethyl, propyl, butyl, etc.), branched (e.g., isopropyl, isobutyl, tertiary butyl, neopentyl, etc.), cyclic (e.g., cyclopropyl, cyclobutyl, cyclopentyl, methylcyclopentyl, cyclohexyl, etc.), or multi-cyclic (e.g., bicyclo[2.2.1]heptane, spiro[2.2]pentane, etc.). The alkane radical may be substituted or unsubstituted. Similarly, the alkyl portion of an alkoxy group or alkanoate have the same definition as above.

"Alkenyl" refers to an acyclic hydrocarbon containing at least one carbon carbon double bond. The alkene radical may be straight, branched, cyclic, or multi-cyclic. The alkene radical may be substituted or unsubstituted.

"Alkynyl" refers to an acyclic hydrocarbon containing at least one carbon carbon triple bond. The alkyne radical may be straight, or branched. The alkyne radical may be substituted or unsubstituted.

"Aryl" refers to aromatic moieties having single (e.g., phenyl) or fused ring systems (e.g., napthalene, anthracene, phenanthrene, etc.). The aryl groups may be substituted or unsubstituted.

"Heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

Within the field of organic chemistry and particularly within the field of organic biochemistry, it is widely understood that significant substitution of compounds is tolerated or even useful. In the present invention, for example, the term alkyl group allows for substituents which is a classic alkyl, such as methyl, ethyl, propyl, hexyl, isooctyl, dodecyl, stearyl, etc. The term specifically envisions and allows for substitutions on alkyls which are common in the art, such as hydroxy, halogen, alkoxy, carbonyl, keto, ester, carbamato, etc., as well as including the unsubstituted alkyl moiety. However, the substituents should be selected so as to not adversely affect the pharmacological characteristics of the compound or adversely interfere with the use of the medicament. Suitable substituents for any of the groups defined above include alkyl, alkenyl, alkynyl, aryl, halo, hydroxy, alkoxy, aryloxy, mercapto, alkylthio, arylthio, mono- and di-alkyl amino, quaternary ammonium salts, aminoalkoxy, hydroxyalkylamino, aminoalkylthio, carbamyl, carbonyl, carboxy, glycolyl, glycyl, hydrazino, guanyl, and combinations thereof.

"Solvate" means an aggregate that comprises one or more molecules of the solute, such as Compound I, with one or more molecules of a solvent, such as water, ethanol, and the like.

"Suitable solvent" refers to any solvent, or mixture of solvents, inert to the ongoing reaction that sufficiently solubilizes the reactants to afford a medium within which to effect the desired anion exchange or salt formation.

"Mixed broth" refers to a conversion mixture where the fermentation broth is treated directly with a deacylating enzyme without purification to produce the deacylated product (e.g. ECBN).

DETAILED DESCRIPTION OF THE INVENTION

Crude mixtures of cyclic peptides described herein may be prepared by fermentation of known microorganisms as described in the art. The subsequent deacylation is typically carried out enzymatically using a deacylase enzyme by known materials and procedures described in the art.

For example, the cyclic peptide I where $R^1$ and $R^4$ are each hydroxy, $R^2$, $R^3$ and $R^7$ are each methyl (i.e., cyclic nucleus corresponding to A-30912A) may be prepared using the procedure detailed in U.S. Pat. No. 4,293,482. The cyclic peptide II(a) where $R^1$ is hydroxy, $R^2$, $R^3$ and $R^7$ are each methyl, and $R^4$ is hydrogen (i.e., cyclic nucleus corresponding to A-30912B) may be prepared using the procedure detailed in U.S. Pat. No. 4,299,763. Aculeacin may be prepared using the procedure detailed in U.S. Pat. No. 3,978,210. The cyclic peptide I where $R^3$ is $CH_2C(O)NH_2$, $R^7$ is methyl, $R^2$ is hydrogen, and $R^1$ and $R^4$ are hydroxy may be prepared using the procedure detailed in U.S. Pat. No. 5,198,421.

Fermentation and mixed broths contain a number of related by-products that are very difficult to separate from the desired cyclopeptide product. Reversed phase, liquid chromatography (RP-LC) has been used in the past with reasonable success; however, the need for higher purity compounds demands even more improved methods of purification.

Products isolated from a mixed broth solution or a fermentation process are generally prefiltered to remove particulates. Prefiltration may be accomplished by any number of means known in the art including gravity filtration, vacuum filtration through a ceramic filter which may or may not include a Celite™ filter aid, etc. Solids in the fermentation broth may also be removed by centrifugation followed by decanting the liquid from the solids. Concentrates from a mixed broth refer to those acquired directly from the filtration or centrifugation of the fermentation mixed broth.

If the filtered solution requires further purification, the concentrated solution may be separated using preparative liquid chromatography prior to any crystallization attempts. Those concentrates that originate from chromatographic partitions serve as an example of solutions from a partially purified process stream and are referred to as a "polished concentrate."

Any chromatographic method well-known in the art may be used to provide the desired separation of products. Preferred chromatographic methods employ the use of reverse-phase media with an acidic elution scheme. Preferably, an eluent containing acetic acid. For example, the material may be purified using the chromatographic method described in Kroeff, et al. filed Dec. 9, 1998 entitled "Purification of Echinocandin Cyclopeptide Compounds." The purification method includes adsorbing the mixture onto a hydrophobic, reversed phase chromatographic media and eluting with a continuous nearly linear acetic acid gradient ranging from 0.1% acetic acid to 10.0% acetic acid by volume in water, preferably from 0.5% (pH=5.5) to 4.0% (pH=2.5) acetic acid.

To crystallize the ECBN salt, the solution from the mixed broth or collected partitions from the chromatographic process are first concentrated. Conventionally, the solution was concentrated by means of an evaporative method (e.g., distillation). However, Applicants have discovered that a nano-filtration system provides a more efficient and higher quality concentrate. The process involves a 200 fold concentration of a dilute (approx. 1 g/liter) solution of the cyclopeptide nucleus on an approximately 400 molecular weight reverse osmosis membrane. The membrane retains the cyclopeptide nucleus while allowing lower molecular weight impurities to pass through. The nano-filtration method provides several advantages over the conventional evaporative methods such as, higher potency, eliminates the need for freeze drying the nucleus, shorter cycle time, and significant reduction of degradation products during concentration. Unlike distillation, nano-filtration allows one to produce a concentrate having a weight percent between about 18 and 22% without significant degradation.

In addition to other related impurities, the fermentation broth for Echinocandin B contains varying levels of a tripeptide-aldehyde (Asn-Gln-Leu-H) by-product having the following chemical structure (Ia). The tripeptide-aldehyde by-product under goes deacylation as well as Echinocandin B during the enzymatic deacylation process to form the corresponding deacylated tripeptide-aldehyde (Ib).

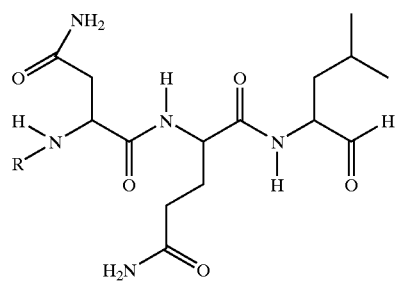

(I)

where R is $C(O)CH_2CH(OH)C_9H_{19}$ (Ia-fermentation by-product) or a hydrogen (Ib-deacylation by-product from a mixed broth).

Surprisingly, the retention time of the deacylated tripeptide-aldehyde is very similar to ECBN in reversed phase, liquid chromatography (RP-LC), even under optimum elution conditions, thus making it very difficult to separate the deacylated tripeptide-aldehyde (Ib) from the desired ECBN. The nano-filtration process also does not sufficiently remove the deacylated tripeptide-aldehyde. It has now been shown that the tripeptide impurity influences the ability to crystallize the ECBN salt. Although not wishing to be bound by any one theory, it is believed that the tripeptide impurity (Ib) forms a weak complex with the ECB Nucleus in solution which serves to decrease, or otherwise inhibit the rate of ECB Nucleus crystallization, thus contributing to poor product recovery. Consequently, the tripeptide by-product is preferably removed or modified prior to the isolation of crystalline ECBN.

The tripeptide-aldehyde by-product may be modified in the ECBN concentrate by reacting the aldehyde with a derivatizing agent prior to crystallization. The derivatizing agent selectively interacts with the aldehyde thus decreasing or eliminating any interaction between the aldehyde and the ECBN. "Derivatizing agent" refers to a reagent capable of interacting (i.e., reaction or complexation) with the aldehyde functionality of the tripeptide by-product to produce an intermediate that is sufficiently different in hydrophobicity to allow separation of the tripeptide intermediate from the desired ECBN salt. For example, the solubility of the aldehyde is increased such that the ECBN salt selectively crystallizes from solution leaving the aldehyde in solution. Suitable derivatizing agents include sodium bisulfite, hydrazine, hydroxyl amine and semicarbazide hydrochloride. At least one equivalent of derivatizing agent is added per equivalent of aldehyde impurity. Preferably, a slight excess of derivatizing agent is added (i.e., approximately 1.2 equivalents).

An organic or inorganic acid is added to the concentrate to adjust the pH of the concentrate solution to less than 4.0, preferably between about 4.0 and 2.0, more preferably between about 3.5 and about 2.5. The optimum pH (i.e., degree of protonation) will depend upon the local chemical environment of the amine function. In other words, the pH is adjusted such that formation of the ammonium salt is favored. The ECBN salt may be crystallized from the acidic concentrate by adding an acid or metal salt containing the desired anion followed by slowly cooling the mixture to initiate crystallization. The acid/metal salt may be added in portions. The portions may be added in equal or unequal amounts. Portion wise addition appears to control the crystal growth process. Typically, the first portion contains nearly twice the amount of the second or third portion. Preferably, the metal salt is added in portions at different temperatures. For example, the first portion of metal salt is added between about 22 and 28° C., the second portion added between about 20 and 15° C., and the third portion added between about 8 and 12° C. Lowering the temperature from 28° C. to about 10° C. helps to decrease the solubility of the ECBN salt and thus assists in the crystallization of the ECBN salt; however, further lowering of the temperature below 10° C. did not appear to significantly effect the solubility of the ECBN salt. The increased amount of acid/metal salt added to the concentrate is believed to not only provide a rich anion source, but also reduces the solubility of the ECBN salt. The total amount of acid/metal salt added to the concentrate is generally between about 14 and 16 weight percent of the concentrate. Preferably, a seed crystal is added to assist the initiation of the crystallization process.

When the cyclopeptide is the nucleus of echinocandin B, the acetate salt is an amorphous solid. Applicants have discovered that the anion of the amorphous ammonium cyclopeptide salt can be easily exchanged in the presence of an alternative anion source (an acid or metal salt) to form a crystalline salt. For example, the HPLC partitions containing the ECBN is typically in the form of an ammonium acetate salt since the eluent is acetic acid. The anion-exchange may be accomplished by adding the appropriate acid/metal salt which serves as the alternative anion source at any step prior to crystallization. For ECBN, a preferred anion source is HCl/sodium chloride.

In summary, the formation of an ECBN salt includes the steps of: (i) concentrating a solution containing ECBN or amorphous salt thereof and an aldehyde impurity using a nanofiltration process; (ii) adding a derivatizing agent (preferably sodium bisulfite) which interacts with the aldehyde impurity; (iii) adjusting the pH to less than 4.0; (iv) adding an acid or metal salt (preferably NaCl); and (v) cooling the mixture to initiate crystallization of the ECBN salt. A seed crystal of ECBN salt may optionally be added to help initiate crystallization. Preferably, the sodium chloride is added in three portions (the first portion is added between about 22 and 28° C.; the second portion is added between about 15 and 20° C.; and the third portion is added between about 8 and 12° C.). In addition, the first portion, preferably, contains nearly twice the amount of sodium chloride by weight as the second or third portion.

The anion of an isolated ECBN salt may be exchanged by slurrying the cyclopeptide ammonium salt with an acid salt (or metal salt) containing the desired anion in a suitable solvent, heating the slurry to dissolve the reactants, and then cooling the solution to form the desired crystalline salt.

The crystalline forms offer several advantages such as easier isolation of the cyclopeptide from the mixed fermentation broth and/or process streams, improved purification of intermediates, improved shelf-life, and increased yields of the final acylated product. The degree to which each of these advantages are realized may be dependent upon the particular salt form and the process by which the salt is produced.

The crystalline salt may be isolated in a variety of crystalline forms (e.g., simple salt and inner-salt forms, solvated and/or hydrated forms, etc.). A simple protonated ammonium salt may be in the form of a mono- or di-acid addition salt, such as CP—$NH_3^+A^-$, (CP—$NH_3^+)_2A^{-2}$, and (CP—$NH_3^+M^+)A^{-2}$ where CP—$NH_3^+$ represents the cyclopeptide containing a protonated primary amino group (e.g., ECBN), A is a mono- or di-valent anion and $M^+$ is a mono-valent metal. Suitable monovalent anions include chloride, bromide, iodide, dihydrogen phosphate, hydrogen sulfate, hydrogen oxalate, hydrogen tartrate, benzoate, methanesulfonate and p-toluenesulfonate. Suitable divalent anions include sulfate, oxalate, hydrogen phosphate, tartrate and fumarate. Suitable metal cations include ammonium, lithium, sodium, potassium and tetraalkylammonium.

Inner-salt forms may be represented by formulae such as (CP—$NH_3^+A^-)(M^+A^-)$ and ((CP—$NH_3^-)_2A^{-2})(M^{+2}A^{-2})$, where $M^{+2}$ is a divalent metal. Suitable divalent metals include calcium and magnesium.

In addition to the basic salt forms discussed above, the salt can be isolated as a solvate. Examples of solvated forms include those with the following chemical formulae: (CP—$NH_3^{+A-})(H_2O)_a(S)_b$ where S is an organic solvent and the subscripts a and b represent solvate stoichiometry. Suitable solvate solvents include methanol, ethanol, ethylacetate, acetone, acetonitrile, tetrahydrofuran and toluene.

The non-solvated and solvated forms may exhibit polymorphism. For example, the crystalline form may be dependent upon the conditions for crystallization. Even though the stoichiometry may be the same, there may exist different three dimensional solid phase crystalline structures with different physical and chemical properties.

It will be understood by those skilled in the art that the following serves as illustrative examples and that other cyclopeptide ammonium salts can be purified or produced using the procedures described below. All references cited herein are hereby incorporated herein by reference.

EXAMPLES

Materials used in the following preparations are available from Aldrich Chemicals (Milwaukee, Wis.) unless designated otherwise. The following abbreviations are used: ACN—acetonitrile; TFA—trifluoroacetic acid; and TRS—total related substances (i.e., impurities)

Analytical Characterization of Samples

The quality and quantity of ECBN filtrate samples were evaluated using the following analytical methods.

Phosphate system: A Zorbox™ SB C-18, 3.5 micron particle column (0.46 cm ID×15 cm), was eluted with a 1.0% phosphoric acid/ACN mobile phase at a flow rate of 1.5 ml/min. The column was operated at 30° C. and the effluent monitored at 210 nm. The column is equilibrated in 1% ACN and after sample injection, a gradient ranging from 5 to 61.0% ACN over 9 minutes was used to elute ECBN. After elution, the column was washed with 50% ACN to elute any highly retained components.

Phosphate/Octanesulfonic Acid (OSA system): This system is similar to the phosphate system discussed above, with the exception that the mobile phase contains 30 mM OSA and 0.2% phosphoric acid. The column is equilibrated with 10% ACN. After the sample is injected, elution of ECBN is accomplished with a gradient ranging from 10 to 28% ACN over 9 minutes. The column was then washed with 50% ACN to elute highly retained components. Column flow rate and detector wavelength were as above, while the column temperature was 50° C. This system is particularly useful for quantitating the Asn-Gln-Leu-H tripeptide-aldehyde component.

TFA system: A Vydac™ C-18, 3.5 micron column (0.46× 25 cm) was used for the assay. The mobile phase contained 0.1% TFA and elution was accomplished using a linear ACN gradient of 0 to 10% over 20 minutes, followed by a column wash of 50%. Column flow rate, temperature, and detector wavelength were the same as for the phosphate system described above.

General Procedures

Nanofiltration Process

Charge 10,000 liters of resin eluate containing approximately 30 Kg of ECBN dissolved in water containing ~3% acetic acid and 5% acetonitrile, to a nanofiltration system equipped with 600 ft² of Millipore Nanomax 50 membranes. The nanofiltration system is operated at 600 psig, 15° C., and a recirculation flowrate of ~50–200 lpm. The solution is concentrated to ~300 liters over 1–3 hours. The pH is adjusted with conc. HCl to between 2.7 and 3.0. The system is diafiltered with ~1000 liters of water (i.e., wash with water, while keeping the total volume roughly constant at 300 liters, e.g., add the water at the same rate that the filtrate flows through the membrane). After washing, the solution is concentrated to a final volume of 100 to 150 liters (200–300 g/liter). This is then taken directly into the crystallization step.

Example 1

Example 1 illustrates the crystallization process and the complexation of tripeptide-aldehyde impurities in a concentrate.

A sample of an assay characterized aqueous ECB Nucleus Concentrate solution from various production lots that had been nanofiltered using the general process described above was weighed. (see Table I for subsequent treatments). In some cases, sodium bisulfite was added and the mixture stirred until the sodium bisulfite had dissolved. In all cases, the pH of the resulting solution was adjusted to 3.2–2.9 with dropwise addition of a dilute solution (~10 wt %) of hydrochloric acid. To the resulting pH adjusted solution was added a calculated quantity of sodium chloride and the mixture was stirred until the solids had dissolved. The resulting solution was transferred to a 100 ml jacketed crystallizer, equipped with a mechanical stirrer. To the stirred solution was added a fixed quantity of crystalline ECB Nucleus seed crystals (690 mg). The resulting seed slurry was stirred at 25° C. for a period of about 24 hours. A second quantity of sodium chloride was added. The temperature of the stirred slurry was adjusted to 17° C. and the contents were stirred for about 24 hours. Finally, a third quantity of sodium chloride was added. The temperature of the stirred slurry was adjusted to 10° C. and the contents were stirred for about 24 hours. The resulting solids, from the ECB Nucleus crystalline slurry, were isolated by vacuum filtration. The crystalline wet cake product was washed with an aqueous solution of sodium chloride (about 10 ml, 14 wgt. %) and pulled dry. The crystals were allowed to dry in a 75% relative humidity chamber, overnight. The isolated products were weighed and assayed for potency as recorded in Table II where * indicates that potency may be low due to insufficient drying.

TABLE I

| Conc. Sample # | Conc Pot (wt %) | Tripep Impur (wt %) | Conc Amt (g) | ECBN Amt (bg) | Na Bisulfite (g) | 1st NaCl (g) | 2nd NaCl (g) | 3rd NaCl (g) |
|---|---|---|---|---|---|---|---|---|
| 3-1a | 21.18 | 7.3 | 55.23 | 11.70 | 0.00 | 4.23 | 1.06 | 0.63 |
| 3-1b | 21.18 | 7.3 | 55.23 | 11.70 | 1.70 | 4.23 | 1.06 | 0.63 |
| 3-1a | 23.85 | 7.9 | 52.01 | 12.40 | 0.00 | 3.99 | 1.00 | 0.60 |
| 3-2b | 23.35 | 7.9 | 52.01 | 12.40 | 1.83 | 3.99 | 1.00 | 0.60 |
| 3-3a | 21.4 | 14.3 | 56.57 | 12.11 | 0.00 | 4.33 | 1.08 | 0.65 |
| 3-3b | 21.4 | 14.3 | 56.57 | 12.11 | 2.42 | 4.33 | 1.08 | 0.65 |
| 3-4a | 22.38 | 11.5 | 55.72 | 12.47 | 0.00 | 4.27 | 1.07 | 0.64 |
| 3-4b | 22.38 | 11.5 | 55.72 | 12.47 | 2.10 | 4.27 | 1.07 | 0.64 |
| 3-5a | 22.83 | 0.9 | 52.75 | 12.04 | 0.00 | 4.04 | 1.01 | 0.61 |
| 3-5b | 22.83 | 0.9 | 52.75 | 12.04 | 1.28 | 4.04 | 1.01 | 0.61 |
| 3-6a | 21.68 | 7.74 | 55.24 | 11.98 | 0.00 | 3.89 | 0.97 | 0.58 |
| 3-6b | 21.68 | 7.74 | 55.24 | 11.98 | 1.28 | 3.89 | 0.97 | 0.58 |

TABLE II

| Sample # | ECBN Yield(g) | ECBN Potency(%) | ECBN Yield(bg) | ECBN Yield(%) |
|---|---|---|---|---|
| 3-1a | 9.01 | 71.7 | 6.46 | 55.2 |
| 3-1b | 11.93 | 74.3 | 8.86 | 75.8 |
| 3-1a | 20.38 | 48.7 | 9.92 | 80.0 |
| 3-2b | 13.1 | 76.4 | 10.01 | 80.7 |
| 3-3a | 4.36 | 75.9 | 3.31 | 27.3 |
| 3-3b | 19.23 | 54* | 10.38 | 85.8 |
| 3-4a | 23.79 | 45.2 | 10.75 | 86.2 |
| 3-4b | 13.23 | 76.8 | 10.16 | 81.5 |
| 3-5a | 12.74 | 76.3 | 9.72 | 80.7 |
| 3-5b | 13.11 | 75.8 | 9.94 | 82.5 |
| 3-6a | 8.38 | 73.8 | 6.18 | 51.6 |
| 3-6b | 11.55 | 75 | 8.66 | 72.3 |

Example 2

Example 2 illustrates the conversion of an amorphous ECBN acetate ammonium salt to a variety of crystalline salts.

A quantity of ECBN ammonium acetate salt (5.0 g, 88.4% potency, 4.15% TRS) was placed into a 50 ml Erlenmeyer screw top flask. A solution of an acid salt in water was then added (Table III where $^1$TRS is the total related substances (e.g., impurities); and $^2$KF is the Karl Fisher Assay). The resulting slurry was stirred to dissolve the solids. A small quantity of seed crystals were added and the flask was sealed. The flask was placed in an orbital shaker bath maintained at −25° C. and shaken for a period of 5 days upon which a precipitate formed. A ⅘ portion of the precipitate was isolated by vacuum filtration. The isolated wet cake was partitioned into two fractions: (A) a wet cake fraction; and (B) a semi-dry fraction. The wet cake fractions were stored in sealed vials.

The semi-dry fraction was washed with a solution of acetonitrile in water (95:5 by volume, 2 ml). The washed cake was dried at ambient temperature and pressure for about 15 minutes (sufficient time for the ACN odor to dissipate). The free flowing semi-dry wet cake powders were stored in sealed vials.

The isolated semi-dry cakes were analyzed for anions and cations by ion chromatography. Potency and impurities (TRS) were determined by high performance liquid chromatography (HPLC).

TABLE III

| Samp No | Salt added | Salt Amt (g) | Salt Conc. Wt % | Crystalline Assay | | | | |
|---|---|---|---|---|---|---|---|---|
| | | | | Pot (%) | TRS$^1$ (%) | KF$^2$ (%) | An (%) | Cat (%) |
| 1 | NaCl | 23.6 | 14.6 | 76.4 | 1.57 | 17.6 | 4.98 | 0.78 |
| 2 | NaCl | 17.7 | 11.0 | 79.9 | 0.83 | 17.6 | 6.70 | 0.61 |
| 3 | Pot. oxa. | 31.9 | 23.1 | 64.1 | 1.66 | 16.1 | 10.4 | 3.29 |
| 4 | Pot. oxa. | 23.9 | 17.3 | 80.9 | 1.05 | 17.0 | 4.92 | 0.75 |
| 5 | NH$_4$SO$_4$ | 26.5 | 33.1 | 74.7 | 1.05 | 16.2 | 8.69 | 1.07 |
| 6 | NH$_4$SO$_4$ | 17.7 | 16.6 | 77.7 | 0.88 | 17.2 | 5.90 | 0.48 |
| 7 | LiSO$_4$ | 35.4 | 20.7 | 76.1 | 0.66 | 17.7 | 7.59 | 0.52 |
| 8 | Na$_2$SO$_4$ | 26.5 | 17.8 | 78.2 | 0.54 | 17.1 | 5.71 | 0.76 |
| 9 | Na$_2$SO$_4$ | 26.5 | 17.8 | 78.9 | 0.55 | 17.2 | 5.36 | 0.56 |
| 10 | NaBr | 10.0 | 21.4 | 76.9 | 0.78 | 15.3 | 9.36 | 0.78 |
| 11 | Amm oxa | 10.0 | satd. | 80.8 | 0.48 | 17.3 | 4.50 | 0.11 |
| 12 | Na oxa | 10.0 | satd. | 81.8 | 0.54 | 17.2 | 2.12 | 0.10 |
| 13 | Na isethionate | 10.0 | 36.1 | 78.2 | 0.58 | 14.1 | 9.10 | 0.44 |
| 14 | NaH$_2$PO$_4$ | 19.7 | 27.0% | 74.2% | 0.67% | 17.5% | 7.25% | 1.25% |
| 15 | NaH$_2$PO$_4$ | 19.7 | 27.0% | 73.7% | 1.48% | 18.3% | 6.59% | 1.25% |

TABLE III-continued

| Samp No | Salt added | Salt Amt (g) | Salt Conc. Wt % | Crystalline Assay | | | | |
|---|---|---|---|---|---|---|---|---|
| | | | | Pot (%) | TRS[1] (%) | KF[2] (%) | An (%) | Cat (%) |
| 16 | NaNO$_3$ | 10.0 | 30.0% | 79.1% | 0.56% | 15.6% | 7.40% | 1.03% |
| 17 | CaCl$_2$ | 10.0 | 25.0% | 75.7% | 1.02% | 18.6% | 5.95% | 1.55% |

The isolated wet cakes for each sample were examined microscopically under polarized light and showed birefringent behavior typical of crystalline materials. In addition, photomicrographs displayed crystalline forms. All of the isolated materials showed distinct diffraction patterns consistent with the presence of crystalline materials when analyzed by x-ray powder diffraction (XRPD).

Example 3

Example 3 compares the quality of ECBN concentrated via distillation (Method A) versus nano-filtration (Method B).

Method A

The combined fractions from column elution (called "mainstream" ~10,000 L) are partially transferred to a distillation apparatus. The volatile components, including acetonitrile, acetic acid and water are partially removed by distillation at reduced pressure. Typical distillation temperatures are between 40° C. and 45° C. Transfer of the mainstream to the distillation apparatus and distillation are continued until the total volume of the concentrate is about 200 L. Typical distillation times are 24 to 36 hours.

Method B

The combined fractions from column elution (~10,000 L) are re-circulated through a nano-filtration apparatus under pressure. During the re-circulation operation, a major portion of the acetonitrile, water and acetic acid are removed. Other impurities are also removed, including calcium and magnesium salts. The removed materials are dissolved in a process stream referred to as the "permeate". The concentrated portion, containing retained materials, is referred to as the "retentate". The re-circulation operation is continued until the volume of the retentate is about 500 L.

Sodium chloride (10 kg), hydrochloric acid (to adjust the pH of the retentate to 3.0) and water (2600 L) are added to the retentate. The retentate mixture is re-circulated through the nano-filtration apparatus until the volume of the retentate is about 200 L. Typical nano-filtration times are about 9 hours.

Observations

ECB Nucleus concentrate solutions prepared by nano-filtration (Method B) are of better quality than solutions prepared by distillation (Method A). HPLC chromatograms of the ECB nucleus materials show that the type and quantities of impurities present are lower or absent in nano-filtered materials prepared by Method B as compared to distilled materials prepared by Method A. For example, the chromatograms show that impurities associated with thermal degradation are significantly greater in concentrates prepared by distillation than concentrates prepared by nano-filtration. The average degradation impurity level in 8 distilled concentrates was 6.5% (mean=7.9%, range=4.72% to 11.1%). Whereas, the average degradation impurity level in 18 nano-filtered concentrates was 3.2% (mean=4.7%, range=0.42% to 8.95%).

Recovery of crystalline ECB Nucleus from ECB Nucleus concentrate solutions prepared by nano-filtration are typically greater than recoveries from concentrate solutions prepared by distillation. The average recovery of crystalline ECB Nucleus from 8 distilled concentrate solutions was 25.6% (mean=25.8%, range=4.0% to 47.6%). By contrast, the average recovery of crystalline ECB Nucleus from 18 nano-filtered concentrates was 60.6% (mean=51.0%, range= 23.3% to 78.7%).

We claim:

1. A method for forming a crystalline echinocandin nucleus salt from its mixed broth or partially purified process streams comprising in the following order the steps of;

providing a solution comprising an echinocandin nucleus or amorphous salt thereof, an aldehyde impurity and a solvent;

concentrating said solution by means of a nanofiltration process to form a concentrate;

adding a derivatizing agent which selectively interacts with said aldehyde impurity;

adjusting the pH of said concentrate to less than 4.0;

adding an acid or metal salt;

and cooling said concentrate to form a crystalline echinocandin nucleus salt.

2. The method of claim 1 further comprising a step (vii) adding a seed crystal to initiate crystallization.

3. The method of claim 1 wherein said echinocandin nucleus is represented by the structure

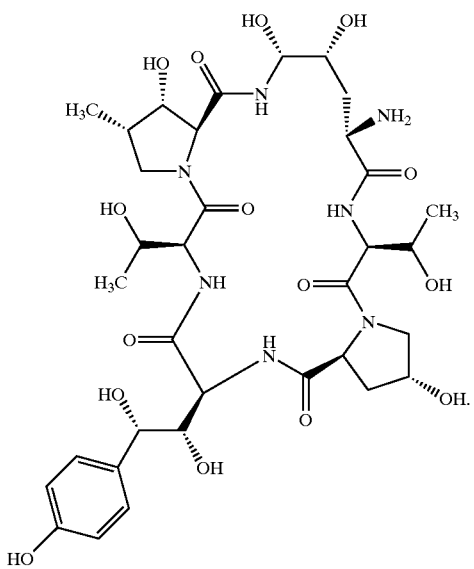

4. The method of claim 3 wherein said derivatizing agent is sodium bisulfite, said acid is hydrogen chloride, and said aldehyde impurity is represented by the structure:

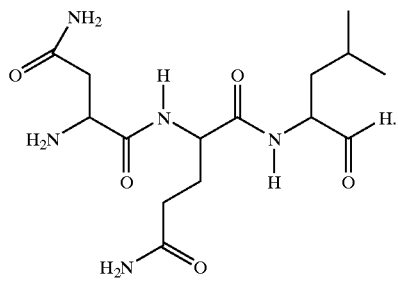

5. The method of claim 1 wherein said metal salt is preferably added in three portions at different temperatures.

6. A crystalline hydrochloride salt of echinocandin B nucleus prepared by the steps of
   providing a solution comprising echinocandin B nucleus or amorphous salt thereof, an aldehyde impurity and a solvent;
   concentrating said solution by means of a nanofiltration process to form a concentrate;
   adding sodium bisulfite;
   adjusting the pH of said concentrate to less than 4.0;
   adding a chloride metal salt; and
   cooling said concentrate.

7. The crystalline hydrochloride salt of claim 6 wherein said chloride metal salt is added in three portions which comprises a first portion which is added between about 22 and 28° C., a second portion which is added between about 20 and 15° C. and a third portion which is added between about 12 and 8° C.

8. The crystalline hydrochloride salt of claim 7 wherein said first portion contains nearly twice as much chloride metal salt by weight as either said second or third portion.

9. A crystalline salt form of a cyclopeptide (CP) echinocandin B nucleus represented by the formula $CP\text{—}NH_3^+$ $A^-$, $(CP\text{—}NH_3^+)_2 A^{-2}$, or $(CP\text{—}NH_3^+ M^+) A^{-2}$ wherein $CP\text{—}NH_3^+$ is represented by the structure

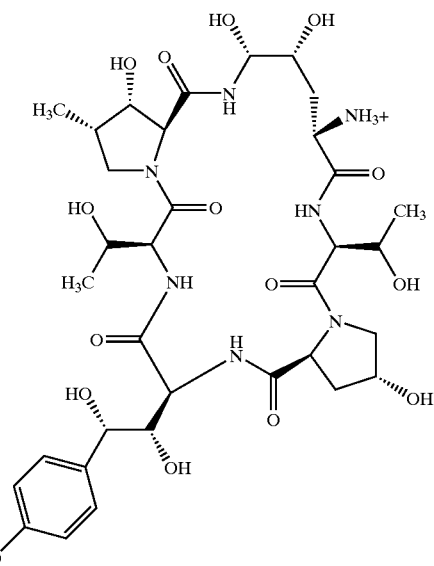

$A^-$ is chloride, bromide, iodide, dihydrogen phosphate, hydrogen sulfate, hydrogen oxalate, hydrogen tartrate, benzoate, methanesulfonate, or p-toluenesulfonate;
$M^+$ is ammonium, lithium, sodium, potassium or tetraalkylammonium,
$A^{-2}$ is sulfate, oxalate, hydrogen phosphate, tartrate or fumarate; and pharmaceutically acceptable solvates or hydrates thereof.

10. A crystalline inner-salt form of a cyclopeptide (CP) echinocandin nucleus represented by the formula (CP—$NH_3^+ A^-)(M^+ A^-)$ or $((CP\text{—}NH_3^+)_2 A^{-2})(M^{+2} A^{-2})$ wherein $CP\text{—}NH_3^+$ is represented by the structure

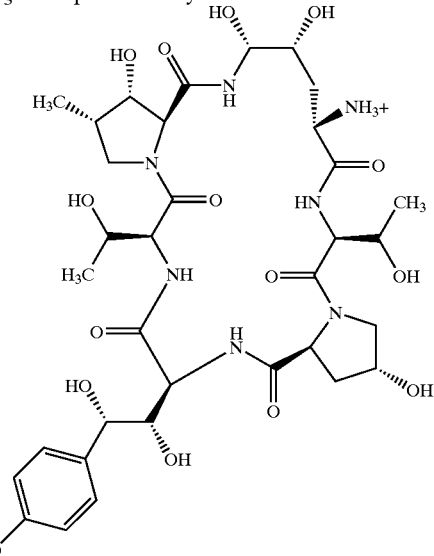

$A^-$ is chloride, bromide, iodide, dihydrogen phosphate, hydrogen sulfate, hydrogen oxalate, hydrogen tartrate, benzoate, methanesulfonate, or p-toluenesulfonate;
$M^+$ is ammonium, lithium, sodium, potassium or tetraalkylammonium;
$A^{-2}$ is sulfate, oxalate, hydrogen phosphate, tartrate or fumarate;
$M^{+2}$ is calcium or magnesium; and
pharmaceutically acceptable solvates or hydrates thereof.

* * * * *